United States Patent [19]
Wada et al.

[11] Patent Number: 6,028,220
[45] Date of Patent: Feb. 22, 2000

[54] PRODUCING ACROLEIN AND ACRYLIC ACID USING A SUPPORTED DUAL ACTIVITY MOLYBDENUM, IRON, AND BISMUTH BASED CATALYST IN A FIXED BED MULTITUBULAR REACTOR

[75] Inventors: Koichi Wada, Kanagawa-ken; Yoshimasa Seo; Akira Iwamoto, both of Yamaguchi-ken; Atsushi Sudo, Gunma-ken; Fumio Sakai, Gunma-ken; Kazuo Shiraishi, Gunma-ken; Hiroyoshi Nowatari, Gunma-ken, all of Japan

[73] Assignee: Nippon Kayaku Kabushiki Kaisha, Tokyo, Japan

[21] Appl. No.: 09/117,461
[22] PCT Filed: Dec. 2, 1997
[86] PCT No.: PCT/JP97/04402
§ 371 Date: Jul. 28, 1998
§ 102(e) Date: Jul. 28, 1998
[87] PCT Pub. No.: WO98/24746
PCT Pub. Date: Jun. 11, 1998

[30] Foreign Application Priority Data

Dec. 3, 1996 [JP] Japan ..................... 8-336298

[51] Int. Cl.$^7$ ..................... C07C 205/00; C07C 51/16
[52] U.S. Cl. ..................... 562/546; 562/531; 562/532; 562/545; 568/479
[58] Field of Search ..................... 562/531, 532, 562/534, 545, 546

[56] References Cited

U.S. PATENT DOCUMENTS 5,276,178  1/1994  Onodera et al. ..................... 562/537
5,719,318  2/1998  Kawajiri et al. .
5,892,108  4/1999  Shiotanai et al. .

FOREIGN PATENT DOCUMENTS 3-294239  12/1991  Japan .
8-3093  1/1996  Japan .

*Primary Examiner*—Gary Geist
*Assistant Examiner*—Robert W. Deemie
*Attorney, Agent, or Firm*—Nields, Lemack & Dingman

[57] ABSTRACT

The present invention concerns a method for producing acrolein and acrylic acid by carrying out vapor phase catalytic oxidation of propylene with molecular oxygen or a gas containing molecular oxygen using a oxidation catalysts comprising Mo, Bi and Fe as an essentially element and a fixed bed multitubular reactor, which comprises a) using a plurality of supported catalysts having different activities, which was obtained, for example, by different calcination method in the production process of the supported catalysts, b) setting a catalyst layer in a reaction tube, which is formed by dividing it into plural portions in the tube axial direction, and c) arranging the aforementioned plural supported catalysts in such order that the activity becomes high toward the outlet from the inlet of the material gas in the reaction tube axial direction.

According to the present invention, the generation of hot spot can be avoided and over oxidation reaction can be avoided and the acrolein and acrylic acid are produced constantly for a prolonged period of time.

14 Claims, No Drawings

PRODUCING ACROLEIN AND ACRYLIC ACID USING A SUPPORTED DUAL ACTIVITY MOLYBDENUM, IRON, AND BISMUTH BASED CATALYST IN A FIXED BED MULTITUBULAR REACTOR

FIELD OF THE INVENTION

This invention relates to a method in which acrolein and acrylic acid are produced by carrying out vapor phase catalytic oxidation of propylene with molecular oxygen or a gas containing molecular oxygen using a fixed bed multitubular reactor.

PRIOR ART

A number of complex oxide catalysts containing molybdenum, bismuth and iron have already been proposed for use in the production of acrolein and acrylic acid by a method in which propylene is subjected to vapor phase catalytic oxidation, and some of them are now industrially used. Their typical examples include those which are disclosed in Japanese Patent Publication (KOKOKU) No. 47-27490 (1972), Japanese Patent Publication (KOKOI(U) No. 47-42241 (1972) and Japanese Patent Publication (KOKOKU) No. 48-1645 (1973).

However, industrial production of acrolein or acrylic acid using these catalysts causes various problems.

One of these problems is generation of a local abnormally high temperature part (hot spot) in the catalyst layer. Generation of the hot spot is caused by the exothermic reaction of said vapor phase catalytic reaction. In order to improve productivity in the industrial production of acrolein and acrylic acid, a means is generally employed in which the concentration of the starting material propylene is increased or the space velocity of the reaction gas is increased, but heat accumulation at the hot spot is increased under such high load reaction conditions. Increase in heat accumulation at the hot spot causes shortened catalyst life, increased formation of by-products due to over oxidation reaction and, in the worst case, runaway reaction.

If the activity of a part of the catalyst wherein the hot spot is generated is decreased, the activity of the whole catalyst is probably lowered due to migration of hot spots to other layers (parts) of the catalyst.

In order to avoid generation of such hot spot or excessive heat accumulation at the hot spot, one must unwillingly accept low productivity or must take a countermeasure for example by reducing the reaction tube diameter, which, however, are economically disadvantageous.

In consequence, various studies have been reported, in order to avoid the aforementioned danger in reaction operations caused by the hot spot to ensure economy in the aforementioned industrial production. For example, a method in which a catalyst wherein the hot spot could be generated is diluted with an inert substance (Japanese Patent Publication (KOKOKU) No. 53-30688 (1978)) and a method in which the catalyst to be used is made into a tubular shape (Japanese Patent Publication (KOKOKU) No. 62-36739 (1987)) have been proposed.

Also, reaction methods have been proposed in which two or more reaction zones are arranged in a reaction tube, and in which the reaction is carried out by packing a plurality of catalysts having different activities. Examples of such a type of methods so far reported include a method in which a plurality of catalysts whose activities are controlled by changing composition of catalytically active components (kind and/or quantity of an alkali metal in particular) are packed in a reaction tube along its axis in such a manner that catalysts having higher activities are arranged toward the outlet side from the inlet side of the material gas (Japanese Patent Publication (KOKOKU) No. 63-38331 (1988)) and a method in which a plurality of catalysts having different occupying volumes are packed in a plurality of reaction zones in such a manner that the occupying volume becomes small toward the outlet side from the inlet side of the reaction tube (Japanese Patent Application Kokai No. 4-217932 (1992)).

However, in the method in which a catalyst is diluted with an inert substance, an intensive effort is required in uniformly mixing the inert substance for dilution with the catalyst, but their uniform packing cannot always be effected by this method, thus not only causing frequent generation of hot spots but also entailing inconvenience in carrying out the reaction, because the position and temperature of the hot spot vary in each reaction tube, so that this is not a satisfactory method as a means to prevent generation of hot spot.

The method in which the activity of catalyst is controlled by making it into a tubular shape cannot also be said as a sufficient means for preventing the generation of hot spots or excessive heat accumulation at the hot spot under high load reaction conditions, namely under conditions of high starting material concentration and high space velocity.

In the method in which the activity of catalyst is controlled by changing kind and/or quantity of an alkali metal, its amount to be added is markedly small in comparison with those of other components, so that extent of activity variation of the catalyst by its adding is extremely large due to the difference of so small its adding quantity or included quantity. In addition, the preparation of the catalyst having the aimed activity becomes more difficult due to the influence of alkali metals slightly contained in other starting materials which are added in large amounts. When a plurality of catalysts having different active components are used, these catalysts show different periodical changes during their use for a prolonged period of time, so that it is necessary to optimize the catalyst layer length, the catalyst activity and the like factors taking the periodical changes into consideration, thus requiring complex operations.

In the method in which a plurality of catalysts having different occupying volumes are packed in a reaction tube in such a manner that the occupying volume becomes small toward its outlet side from the inlet side of the reaction tube, thereby arranging a plurality of reaction zones in the axial direction of the reaction tube, it is necessary to control the ratio of occupying volumes of adjacent two reaction zones within a specified range, and it also requires further complex operations in achieving its optimization when the shape, composition and the like factors of the catalysts are different from one another, in addition to the occupying volumes of the catalysts to be used.

The present invention contemplates resolving the aforementioned problems in the prior art, thereby providing a method by which acrolein and acrylic acid can be produced from propylene with a high efficiency.

That is, it contemplates providing a method in which acrolein and acrylic acid are produced by subjecting propylene to vapor phase catalytic oxidation under high load reaction conditions, which is a simple and easy method that can effect the production stably for a prolonged period of time by inhibiting generation of hot spots or excessive heat accumulation at the hot spot of the catalyst layer, obtaining the products of interest with high yields and preventing the catalyst from its deterioration by thermal load.

PRIOR ART

In the exothermic reaction such as the case of the vapor phase catalytic oxidation reaction, catalytically active components are generally used by molding them into various shapes which components are mostly occupied by the catalytically active components. Since the catalyst can be regarded as the reaction field of vapor phase catalytic oxidation, the exothermic reaction occurs exactly on the catalyst. Thus, the heat generated by the reaction is concentrated to induce generation of hot spots. In view of the above, the inventors of the present invention have conducted intensive studies with the aim of obtaining the products of interest stably for a prolonged period of time by avoiding the concentration of heat of reaction generated on the catalyst, and found as a result of the efforts that the aforementioned object can be achieved when a plurality of supported catalysts, having different activities, which are prepared by supporting a suitable amount of a powder that contains catalytically active components to be supported (coated) on an inert carrier and by differing the calcining procedure at preparing the catalysts or the supporting amount of the catalyst, are used by arranging them in a specified manner.

Accordingly, the present invention relates to following (1) to (12)

(1) a method for producing acrolein and acrylic acid by carrying out vapor phase catalytic oxidation of propylene with molecular oxygen or a gas containing molecular oxygen using a oxidation catalysts comprising Mo, Bi and Fe as an essentially element and a fixed bed multitubular reactor, which comprises
a) using a plurality of supported catalysts having different activities,
b) setting a catalyst layer in a reaction tube, which is formed by dividing it into plural portions in the tube axial direction, and
c) arranging the aforementioned plural supported catalysts in such order that the activity becomes high toward the outlet from the inlet of the material gas in the reaction tube axial direction, (2) the method according to the above item (1) wherein plural catalysts having different activities, are prepared whose activity is controlled by means of the calcining treatment in the catalysts preparing process, (3) the method according to the above item (1) or (2) wherein the plural supported catalysts having different activities, comprises at least one element selected from a group of potassium, rubidium, thallium and cesium as an essential element of catalyst active components and the included amount of the components is substantially same in the plural supported catalysts having different activities, (4) the method according to the above item (2) wherein the supported plural catalysts having different activities, are calcined in different temperature selected form 450~650° C. for every supported catalyst, (5) the method according to the above item (1) or (2) wherein the ratio of the supported component including catalytically active components (total supporting ratio) of the plural supported catalysts having different activities, is 10~60% by weight based on total weight of the catalyst, (6) the method according to the above item (5) wherein the supported plural catalysts having different activities, are obtained by using a molding additive and/or a strength improving agent when the supported catalysts are prepared, (7) the method according to any one of the above items (1), (2), (4) and (6) wherein the plural supported catalysts having different activities comprises at least one element selected from a group of potassium, rubidium, thallium and cesium as an essential element of catalyst active components, the included amount of the components is substantially same in the plural supported catalysts having different activities, and the ratio of the supported component including catalytically active components (total supporting ratio) of the plural supported catalysts having different activities, is 10~60% by weight based on total weight of the catalyst, (8) the method according to the above item (7) wherein the composition of the catalytically active components, is represented by the following formula

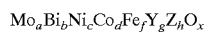

(wherein Mo, Bi, Ni, Co and Fe represent molybdenum, bismuth, nickel, cobalt and iron, respectively, Y is at least one element selected from the group of tin, zinc, tungsten, chromium, manganese, magnesium, antimony and titanium, Z is at least one element selected from the group of potassium, rubidium, thallium and cesium, and a, b, c, d, f, g, h and x represent the number of atoms of molybdenum, bismuth, nickel, cobalt, iron, Y, Z and oxygen, respectively, a=12, b=0.1 to 7, c+d=0.5 to 20, f=0.5 to 8, g=0 to 2, h=0 to 1 and x is determined by the oxidized condition of each element)
in the plural supported catalysts having different activities, (9) the method according to any one of the above items (1), (2), (4), (6) and (8) wherein the carrier of the plural supported catalysts having different activities, is the same,

(10) the method according to any one of the above items (1), (2), (4), (6) and (8) wherein the composition of the catalytically active component of the plural supported catalysts having different activities, is the same,

(11) the method according to any one of the above items (1), (2), (4), (6) and (8) wherein an amount of the carrier of the plural supported catalysts having different activities, is at least 20% by weight based on the sum of the weight of the supported catalysts, and

(12) the method according to any one of the above items (1), (2), (4), (6) and (8) wherein the plural supported catalysts having different activities, which are obtained by calcining the lower temperature or whose supporting amount are the more, are arranged at the nearer position of the outlet.

The plural supported catalysts having different activities in present invention means the supported catalysts having different reactivity of propylene (conversion ratio) per unit time when they are loaded in a same reaction tube with same volume and reacted under same condition.

The method disclosed in Japanese Patent Application Kokai No. 4-217932 (1992) which uses the same catalysts composition obtained by the same manner whose occupying volumes are varied by differing their supporting amounts, is seemed to be a same method which comprises using the supported catalysts whose activities are varied by differing their catalyst suppoting amounts of the present invention. The method disclosed in the described patent, however, comprises the catalysts having the larger occupying ratio (the more supporting amount) being arranged the nearer to the inlet. The method in the present invention comprises the catalysts having the more supporting amount which have the higher activities, being arranged to the outlet, is quite contrary to the method of the prier art.

BEST MODE FOR CARRYING OUT THE INVENTION

The following describes the present invention in detail.

The oxidation catalyst component to be supported on the carrier is not limited whichever the components comprises molybdenum, bismuth and iron as generally being used for production of acrolein and acrylic acid. Such catalyst component are much disclosed in the U.S. Pat. Nos. 3,454,630, 3,778,386 and Japanese patents described before. The supported catalysts to be used in the present invention which are supporting the oxidation catalysts component disclosed in those prior arts, on an inert carrier can be obtained usually by a method in which catalytically active components that contain a powder of catalytically active components are supported on an inert carrier by a generally method described bellow and then calcined.

The favorable catalysts in the present invention are catalytically active components having a composition of the following formula is supported on a carrier.

$$Mo_aBi_bNi_cCo_dFe_fY_gZ_hO_x$$

(In this formula, Mo, Bi, Ni, Co and Fe represent molybdenum, bismuth, nickel, cobalt and iron, respectively, Y is at least one element selected from the group of tin, zinc, tungsten, chromium, manganese, magnesium, antimony and titanium, Z is at least one element selected from the group of potassium, rubidium, thallium and cesium, and a, b, c, d, f, g, h and x represent the number of atoms of molybdenum, bismuth, nickel, cobalt, iron, Y, Z and oxygen, a=12, b=0.1 to 7, c+d=0.5 to 20, f=0.5 to 8, g=0 to 2, h=0 to 1 and x is determined by the oxidized condition of each element.) In the above definition, it is desirable that a=12, b=0.5 to 4, c+d=1 to 12, f=0.5 to 5, g=0 to 1 and h=0.01 to 0.5. The powder containing catalytically active component to be supported on a carrier, is prepared by a coprecipitation, spray drying or the like means, using nitrate, ammonium salt, hydroxide, oxide, acetate and the like salts of respective metal elements as the starting materials with no particular limitation. The powder containing catalytically active components is usually subjected to preliminary calcination at a temperature of from 200 to 600°C., preferable 300 to 500° C. for from 2 to 24 hours prior to its supporting on a carrier. The preliminary calcination is carried out preferably in the atmosphere of air or in a stream of nitrogen. The thus obtained powder by the preliminary calcination is called preliminarily calcined powder hereinafter. In addition, in production of a plurality of catalysts having different activities, when the catalysts having different activities are obtained by differing the catalytically active component itself or its composition ratio, it is also necessary that the composition of the catalytically active component of the supported catalysts (the case after preliminarily calcination and before supporting, the composition of the preliminarily calcined powder) (the composition of aforementioned formula) is differed, but the same composition of the catalytically active component is favorable because of the production becomes convenient.

When the preliminarily calcined powder described above is supported on a carrier, it is desirable to mix it with a molding additive and/or a strength improving agent. Illustrative examples of the molding additive include crystalline cellulose, starch, stearic acid and the like, and those of the strength improving agent include ceramic fibers, carbon fibers, whiskers and the like. The molding additive or strength improving agent is used in an amount of 30% by weight or less based on the preliminarily calcined powder.

The molding additive and/or strength improving agent may be mixed in advance with the aforementioned preliminarily calcined powder prior to molding or, as will be described later, may be added to a molding machine simultaneously with or before or after the addition of the preliminarily calcined powder and the like.

It is desirable to use a binder when the preliminarily calcined powder is supported on the carrier. Illustrative examples of the binder include water, an alcohol, a polyhydric alcohol such as glycerol or the like or a mixture thereof. The binder is used in an amount of from 10 to 60% by weight based on the preliminarily calcined powder.

Any material can be used as the carrier as long as it is inert and porous or can be made into porous granules, and its examples include (α-alumina, silicon carbide, pumice, silica, zirconium oxide, titanium oxide and the like. The carrier can be made into spherical, cylindrical, tubular and the like shapes with no specific limitation, but is particularly desirable when production efficiency and mechanical strength of the catalyst are taken into consideration. When the shape of the carrier is spherical, the carrier may have a particle size of preferably from 3 to 12 mm. Types of the carrier for a plurality of catalysts may be the same or different from one another, but they may preferably be the same.

The powder that contains the catalytically active components (the powder containing preliminarily calcined powder, if necessary further containing a molding additive and/or a strength improving agent, to be referred to as catalytically active component-containing powder hereinafter) can be supported on the carrier by any method such as a tumbling granulation method, a method using a centrifugal fluidized bed coating apparatus and a wash coating method, with no particular limitation, but the tumbling granulation method is desirable when catalyst production efficiency and the like are taken into consideration. Illustratively, this is a method in which a fixed cylindrical container whose bottom part is equipped with a disc having even or irregular surface is used, and a carrier charged in the container is vigorously mixed through the repetition of rotation and revolution effected by high speed spinning of the disc, to which the catalytically active component-containing powder and, if necessary, a binder are added so that said powder is supported on the carrier.

A plurality of catalysts having different activities whose composition of the catalytically active component (the composition represented by aforementioned formula) is the same, may be obtained by differing a kind or amounts of a molding additive, a strength improving agent, and a binder which are added when the catalytically active component-containing powder is supported on the carrier. For example, when the ceramic fibers which are not burned out in the calcination after supporting, are used by differing their amount largely, concentration of the catalytically active component which are supported on the carrier is differed and thus catalysts having different activities may be obtained.

The ratio of the catalytically active component to the whole of the calcined catalyst may be differed with much extent of 5 to 80% by weight and the ratio is preferable 10 to 60% by weight and more preferable 20 to 55% by weight. When an any other component except of the catalytically active component to be supported on the carrier, for example, a molding additive or inert diluting material which are remained after the calcination, the ratio of the whole supported material (the ratio of the whole supported amount) is preferable within abovementioned ratio.

In the present invention, when the supported amount is larger, the activity of the catalysts becomes higher because the size of the inert carrier is relatively larger (more than 20% by weight, preferable more than 30% by weight, more preferable more than 40% by weight (weight of the carrier/weight of the supported catalysts)) and relatively smaller amount of active catalysts are supported compared to the supported catalysts disclosed in Japanese Patent Application Kokai No. 4-217932 (1992).

In this connection, the supported amount is represented by "weight of catalytically active components/(weight of catalytically active components+weight of carrier+weight of strength improving agent after calcination (optional component)", and is referred to as catalyst supported ratio hereinafter. The term "weight of catalytically active components" as used herein means weight of the catalytically active components after calcination and because of it being not so different to weight of the preliminarily calcined powder, the weight of the preliminarily calcined powder was used for calculation in this specification.

The calcination temperature after supporting catalytically active component-containing powder on the carrier, is preferably from 450 to 650° C., more preferably from 480 to 600° C.

Because the activity of the catalysts used in present invention becomes higher, when the calcination temperature or the calcination time is reduced, and becomes lower when calcination temperature or calcination time is increased, a plurality of catalysts having different activities are prepared by differing the calcination temperature and/or calcination time. This method is remarkably preferable for production of catalysts because a plurality of catalysts having different activities is obtained by same process before calcination.

The calcination time is generally from 3 to 30 hours, preferably from 4 to 15 hours. The preferred combination of calcination temperature and time is varied depending on the supported amount or the kind of catalytically active components and so on. For example, when the catalyst layer is divided into two parts a catalyst prepared by calcination at 500–650° C. for 4–15 hours is preferably combined with a catalyst prepared by calcination at 450–550° C. for 4–10 hours while the catalyst layer is divided into three parts a catalyst prepared by calcination at 500–650° C. for 4–15 hours is preferably combined with a catalyst prepared by calcination at 500–580° C. for 4–15 hours and a catalyst prepared by calcination at 450–550° C. for 4–10 hours.

The difference of the calcination temperature between these catalysts, is generally less than 100° C., preferably 60° C. In case that the activity is adjusted by differing the calcination time, the calcination temperature may be same, but it is preferable to combine a plurality of catalysts having different activities obtained by calcining at difference of the calcination temperature being above 5° C., preferably 10° C., more preferably 15° C.

The size of supported catalyst as obtained above, is variable depending on the size of the carrier, whole supporting amount and so on. When the shape of the supported catalysts is spherical, the mean diameter of the supported catalysts being used is generally 3–16 mm, preferably 3.5–8 mm. The particle size of the catalysts to be used is determined by taking inner diameter of the reaction tube and the like into consideration. In the case of the catalysts to be used in the present invention in which the same carrier is used for a plurality of catalysts having different activities, size (volume) of the catalysts becomes large as the amounts to be supported increase, when the catalytically active components are supported on the carrier under the same conditions but it is preferable in the present invention to use catalysts whose volume are not so difference. The difference of the catalysts volume is within 2 times, preferably within 1.5 times in case of generally used catalysts. When the shape of the catalysts is spherical, it is preferable to use the catalysts whose difference of particle size is within 30%, preferable 20%.

According to the present invention, a fixed bed multitubular reactor is used as the reactor, and the number of reaction tubes, the packing length of the catalyst, the number of divided portions of catalyst layer and the like vary depending on the operation conditions, so that these factors may be decided in each case in such a manner that optimum operation results are obtained. With regard to the division of catalyst layer, prevention of the generation of hot spots or heat accumulation in the hot spot becomes easy as the number of divided portions increases, but the object can be achieved practically by dividing it into 2 to 3 portions.

Inner diameter of the reaction tube is generally from about 15 to 50 mm. For example, when the inner diameter of reaction tube is 21 to 27 mm in that case, it is desirable to use a combination of catalysts having a particle size of 3.5 to 8 mm whose activities are controlled by adjusting the supported amount in the catalysts to 15 to 60% by weight, and the calcination temperature to 480 to 580° C.

The production method of the present invention may be applied to a once-through (one-pass) operation method or a recycling method, and can be carried out under conditions generally used on them. For example, the reaction to obtain acrolein and acrylic acid may be carried out by introducing a mixture gas consisting of 1 to 10% by volume, preferably 4 to 9% by volume, of propylene as the starting material, 3 to 20% by volume, preferably 4 to 18% by volume, of molecular oxygen, 0 to 60% by volume, preferably 4 to 50% by volume, of water vapor and 20 to 80% by volume, preferably 30 to 60% by volume, of an inert gas (nitrogen, carbon dioxide or the like) onto the aforementioned catalysts at a temperature of 250 to 450° C., under a pressure of atmospheric pressure to 10 atm and at a space velocity (=material gas flow volume/apparent volume of packed catalysts) of 300 to 5,000 $hr^{-1}$.

According to the present invention, run away reaction caused by the generation of hot spot and over oxidation reaction can be avoided and constant operation can be made for a prolonged period of time without employing industrially disadvantageous methods, even under high load reaction conditions in which concentration of the starting material is increased and/or the space velocity is increased, so that the method of the present invention is an outstandingly superior method in comparison with the prior art methods.

When the reaction is carried out according to the present invention by supporting a catalytically active component-containing powder on a carrier, calcining the resultant and then packing a plurality of the thus obtained catalysts having different activities in each of a plurality of reaction zones arranged in the reaction tube axial direction in such order that the catalyst with lower activity is placed from the inlet of the starting material, the danger of causing runaway reaction due to the generation of hot spots or heat accumulation at the hot spot can be avoided and formation of by-products due to over oxidation reaction can be prevented, even under high load reaction conditions, so that the intended acrolein and acrylic acid can be obtained with high selectivity and high yield. The productivity can also be improved markedly, because deterioration of the catalyst due to locally exceeded thermal load can be prevented and the catalyst therefore can be used stably for a prolonged period of time.

Thus, the production method of the present invention is a markedly useful method for the production of acrolein and acrylic acid.

EXAMPLES

The present invention is described further illustratively with reference to the following examples.

The conversion ratio, the selectivity and the yield per pass in the present invention are defined as follows.

Propylene conversion ratio (mol %)=(mol number of reacted propylene)/(mol number of supplied propylene)×100

Total selectivity (mol %)=(mol number of formed acrolein and acrylic acid)/(mol number of reacted propylene)×100

Yield (mol %)=(mol number of formed acrolein or acrylic acid)/(mol number of supplied propylene)×100

Example 1

(Preparation of Catalyst-1)

An aqueous solution (A) was obtained by dissolving 423.8 g of ammonium molybdate and 2.02 g of potassium nitrate in 3,000 ml of distilled water which was heated and stirred.

Separately from this, an aqueous solution (B) was prepared by dissolving 302.7 g of cobalt nitrate, 162.9 g of nickel nitrate and 145.4 g of ferric nitrate in 1,000 ml of distilled water, and an aqueous solution (C) by dissolving 164.9 g of bismuth nitrate in 200 ml of distilled water which had been acidified by adding 25 ml of concentrated nitric acid. The aqueous solutions (B) and (C) were mixed, and the mixture solution was added dropwise to the aqueous solution (A) which was vigorously stirred.

The thus formed suspension was dried using a spray dryer and subjected to 3 hours of preliminary calcination at 440° C., thereby obtaining 570 g of preliminarily calcined powder. Thereafter, 200 g of the preliminarily calcined powder was mixed with 10 g of crystalline cellulose as a molding additive, and thus a mixture of the preliminarily calcined powder and the crystalline cellulose was obtained.

A 300 g portion of alumina carrier having an average particle size of 3.5 mm was put into a tumbling granulator and then the just described mixture and 90 g of 33% by weight glycerol aqueous solution as a binder were simultaneously added thereto to effect support of the mixture on the carrier, thereby obtaining particles having a supported ratio of 40% by weight (to be referred to as active component-supported particles hereinafter).

The active component-supported particles were dried at room temperature for 15 hours and then calcined at 560° C. for 5 hours in the flow of air to obtain a catalyst (1). The catalyst (1) was found to have an average particle size of 4.0 mm, and the composition of its catalytically active components, excluding oxygen, was Mo=12, Bi=1.7, Ni=2.8, Fe=1.8, Co=5.2 and K=0.1 in atomic ratio.

(Preparation of Catalyst-2)

A 300 g portion of the preliminarily baked powder obtained in Preparation of catalyst-1 was mixed with 15 g of crystalline cellulose as a molding additive, and thus obtained a mixture of the preliminarily clcined powder and the crystalline cellulose was obtained.

A 300 g portion of alumina carrier having an average particle size of 3.5 mm was put into a tumbling granulator and then the above-mentioned mixture and 135 g of 33% by weight glycerol aqueous solution as a binder were simultaneously added thereto to effect support of the mixture on the carrier, thereby obtaining particles having a supported ratio of 50% by weight.

The thus obtained active component-supported particles were dried at room temperature for 15 hours and then calcined at 520° C. for 5 hours in the flow of air to obtain a catalyst (2). The catalyst (2) was found to have an average particle size of 4.1 mm, and the composition of its catalytically active components, excluding oxygen, was Mo=12, Bi=1.7, Ni=2.8, Fe 1.8, Co=5.2 and K=0.1 in atomic ratio.

(Oxidation Reaction)

The aforementioned catalysts (1) and (2) were packed in a reaction tube of 21 mm in inner diameter and 5 m in length made of stainless steel (SUS 304) and equipped with a thermocouple, in respective packed layer lengths of 105 cm and 295 cm at central area of the reaction tube starting from the starting material gas inlet toward the outlet. While keeping the reaction bath temperature at 337° C. and the catalyst layer inlet pressure at 1.53 kg/cm$^2$ G, the reaction was carried out by passing a mixture gas consisting of 8% by volume of propylene 14% by volume of oxygen, 25% by volume of water vapor and 53% by volume of nitrogen through the tube at a space velocity of 1,860 hr-1. In this case, maximum temperatures of the catalyst layers starting from the inlet were 388° C. and 400° C., respectively, the propylene conversion ratio was 97.1%, the acrolein yield was 80.9%, the acrylic acid yield was 8.1% and the total selectivity for acrolein and acrylic acid was 91.7%, and decrease in reaction performance was not observed even after continuation of the reaction for 1,000 hours or more.

Example 2

(Preparation of Catalyst-3)

A catalyst (3) was obtained in the same manner as described in Preparation of catalyst-1, except that the calcining temperature was changed to 540° C. The catalyst (3) was found to have an average particle size of 4.0 mm, and the composition of its catalytically active components, excluding oxygen, was Mo=12, Bi=1.7, Ni=2.8, Fe=1.8, Co=5.2 and K=0.1 in atomic ratio.

(Oxidation Reaction)

The aforementioned catalysts (3) and (2) were packed in a reaction tube of 21 mm in inner diameter and 5 m in length made of stainless steel (SUS 304) and equipped with a thermocouple, in respective packed layer lengths of 105 cm and 295 cm starting from the starting material gas inlet toward the outlet. While keeping the reaction bath temperature at 333° C. and the catalyst layer inlet pressure at 1.17 kg/cm$^2$ G, the reaction was carried out by passing a mixture gas consisting of 8% by volume of propylene, 14% by volume of oxygen, 25% by volume of water vapor and 53% by volume of nitrogen through the tube at a space velocity of 1,550 hr-1. In this case, maximum temperatures of the catalyst layers starting from the inlet were 401° C. and 373° C., respectively, the propylene conversion ratio was 98.1%, the acrolein yield was 81.3%, the acrylic acid yield was 8.6% and the total selectivity for acrolein and acrylic acid was 91.6%, and decrease in reaction performance was not observed even after continuation of the reaction for 1,000 hours or more.

Example 3

(Preparation of Catalyst-4)

A 100 g portion of the preliminarily calcined powder obtained in Preparation of catalyst-1 was mixed with 5 g of crystalline cellulose as a molding additive, and thus a mixture of the preliminarily calcined powder and the crystalline cellulose was obtained.

A 300 g portion of alumina carrier having an average particle size of 4 mm was put into a tumbling granulator and then the just described mixture and 45 g of 33% by weight glycerol aqueous solution as a binder were simultaneously added thereto to effect support of the mixture on the carrier, thereby obtaining particles having a supported ratio of 25% by weight.

The thus obtained active component-supported particles were dried at room temperature for 15 hours and then calcined at 520° C. for 5 hours in the flow of air to obtain a catalyst (4). The catalyst (4) was found to have an average particle size of 4.3 mm, and the composition of its catalytically active components, excluding oxygen, was Mo=12, Bi=1.7, Ni=2.8, Fe=1.8, Co=5.2 and K=0.1 in atomic ratio.
(Preparation of Catalyst-5)

A 150 g portion of the preliminarily calcined powder obtained in Preparation of catalyst-1 was mixed with 7.5 g of crystalline cellulose as a molding additive, and thus a mixture of the preliminarily calcined powder and the crystalline cellulose was obtained.

A 300 g portion of alumina carrier having an average particle size of 4 mm was put into a tumbling granulator and then the described mixture and 70 g of 33% by weight glycerol aqueous solution as a binder were simultaneously added thereto to effect support of the mixture on the carrier, thereby obtaining particles having a supported ratio of 33% by weight.

The thus obtained active component-supported particles were dried at room temperature for 15 hours and then calcined at 520° C. for 5 hours in the flow of air to obtain a catalyst (5). The catalyst (5) was found to have an average particle size of 4.5 mm, and the composition of its catalytically active components, excluding oxygen, was Mo=12, Bi=1.7, Ni=2.8, Fe=1.8, Co=5.2 and K=0.1 in atomic ratio.
(Preparation of Catalyst-6)

A 200 g portion of the preliminarily calcined powder obtained in Preparation of catalyst-1 was mixed with 10 g of crystalline cellulose as a molding additive, and thus a mixture of the preliminarily calcined powder and crystalline cellulose was obtained.

A 300 g portion of alumina carrier having an average particle size of 4 mm was put into a tumbling granulator and then the described mixture and 90 g of 33% by weight glycerol aqueous solution as a binder were simultaneously added thereto to effect support of the mixture on the carrier, thereby obtaining particles having a supported ratio of 40% by weight.

The thus obtained active component-supported particles were dried at room temperature for 15 hours and then calcined at 520° C. for 5 hours in the flow of air to obtain a catalyst (6). The catalyst (6) was found to have an average particle size of 4.5 mm, and the composition of its catalytically active components, excluding oxygen, was Mo=12, Bi=1.7, Ni=2.8, Fe=1.8, Co=5.2 and K=0.1 in atomic ratio.
(Oxidation Reaction)

The aforementioned catalysts (4), (5) and (6) were packed in a reaction tube of 27 mm in inner diameter and 5 m in length made of stainless steel (SUS 304) and equipped with a thermocouple, in respective packed layer lengths of 100 cm, 100 cm and 150 cm starting from the starting material gas inlet toward the outlet. While keeping the reaction bath temperature at 334° C. and the catalyst layer inlet pressure at 1.35 kg/cm$^2$ G, the reaction was carried out by passing a mixture gas consisting of 7% by volume of propylene, 13% by volume of oxygen, 10% by volume of water vapor and 70% by volume of nitrogen through the tube at a space velocity of 1,800 hr-1. In this case, maximum temperatures of the catalyst layers starting from the inlet were 404° C., 385° C. and 352° C., respectively, the propylene conversion ratio was 96.6%, the acrolein yield was 84.2%, the acrylic acid yield was 6.2% and the total selectivity for acrolein and acrylic acid was 93.6%, and decrease in reaction performance was not observed even after continuation of the reaction for 1,000 hours or more.

Example 4

The reaction was carried out in the same manner as described in Example 3, except that the space velocity was changed to 1,500 hr-1, the reaction bath temperature to 332° C. and the catalyst layer inlet pressure to 1.1 kg/cm$^2$ G. In this case, maximum temperatures of the catalyst layers were 398° C., 381° C. and 350° C., respectively, the propylene conversion ratio was 96.4%, the acrolein yield was 84.3%, the acrylic acid yield was 6.0% and the total selectivity for acrolein and acrylic acid was 93.6%, and decrease in the reaction performance was not observed even after continuation of the reaction for 1,000 hours or more.

Example 5

(Preparation of Catalyst-7)

A 200 g portion of the preliminarily calcined powder obtained in Preparation of catalyst-1 was mixed with 10 g of crystalline cellulose as a molding additive, and thus a mixture of the preliminarily calcined powder and the crystalline cellulose was obtained.

A 300 g portion of alumina carrier having an average particle size of 4 mm was put into a tumbling granulator and then the described mixture and 90 g of 33% by weight glycerol aqueous solution as a binder were simultaneously added thereto to effect support of the mixture on the carrier, thereby obtaining particles having a supported ratio of 40% by weight.

The thus obtained active component-supported particles were dried at room temperature for 15 hours and then calcined at 550° C. for 5 hours in the flow of air to obtain a catalyst (7). The catalyst (7) was found to have an average particle size of 4.5 mm, and the composition of its catalytically active components, excluding oxygen, was Mo=12, Bi=1.7, Ni=2.8, Fe=1.8, Co=5.2 and K=0.1 in atomic ratio.
(Oxidation Reaction)

The aforementioned catalysts (7) and (6) were packed in a reaction tube of 21 mm in inner diameter and 5 m in length made of stainless steel (SUS 304) and equipped with a thermocouple, in respective packed layer lengths of 105 cm and 295 cm starting from the starting material gas inlet toward the outlet. While keeping the reaction bath temperature at 339° C. and the catalyst layer inlet pressure at 1.81 kg/cm$^2$ G, the reaction was carried out by passing a mixture gas consisting of 8% by volume of propylene, 14% by volume of oxygen, 25% by volume of water vapor and 53% by volume of nitrogen through the tube at a space velocity of 1,860 hr-1. In this case, maximum temperatures of the catalyst layers starting from the inlet were 406° C. and 397° C., respectively, the propylene conversion ratio was 97.4%, the acrolein yield was 79.9%, the acrylic acid yield was 8.9% and the total selectivity for acrolein and acrylic acid was 91.2%, and decrease in reaction performance was not observed even after continuation of the reaction for 1,000 hours or more.

Usage in the Industry

According to the present invention, run away reaction caused by the generation of hot spot and over oxidation reaction can be avoided and constant operation can be made for a prolonged period of time without employing industrially disadvantageous methods, even under high load reaction conditions in which concentration of the starting material is increased and/or the space velocity is increased, so that the method of the present invention is an outstandingly usable method for production of acrolein and acrylic acid.

What is claimed is:

1. A method for producing acrolein and acrylic acid by carrying out vapor phase catalytic oxidation of propylene with molecular oxygen or a gas containing molecular oxygen using oxidation catalysts comprising Mo, Bi and Fe as an element and a fixed bed multitubular reactor, which comprises a) using a plurality of supported catalysts having different activities depending on an amount of catalyst supported on a carrier, b) setting a plurality of catalyst layers within a reaction tube, which is formed by dividing it into plural portions in the tube axial direction, and c) arranging the catalyst layers in such order that the activity of the catalyst in each said layer becomes high toward the outlet from the inlet of the material gas in the reaction tube axial direction.

2. The method according to claim 1 wherein the plural supported catalysts having different activities, comprises at least one element selected from a group of potassium, rubidium, thallium and cesium as an essential element of catalyst active components and the included amount of the components is substantially same in the plural supported catalysts having different activities.

3. The method according to claim 1 wherein the ratio of the supported component including catalytically active components (total supporting ratio) of the plural supported catalysts having different activities, is 10~60% by weight based on total weight of the catalyst.

4. The method according to claim 3 wherein the supported plural catalysts having different activities, are obtained by using a molding additive and/or a strength improving agent when the supported catalysts are prepared.

5. The method according to any one of claims 1 or 4 wherein the plural supported catalysts having different activities comprises at least one element selected from a group of potassium, rubidium, thallium and cesium as an essential element of catalyst active components, the included amount of the components is substantially same in the plural supported catalysts having different activities, and the ratio of the supported component including catalytically active components (total supporting ratio) of the plural supported catalysts having different activities, is 10~60% by weight based on total weight of the catalyst.

6. The method according to claim 5 wherein the composition of the catalytically active components, is represented by the following formula $Mo_aBi_bNi_cCo_dFe_fY_gZ_hO_x$ (wherein Mo, Bi, Ni, Co and Fe represent molybdenum, bismuth, nickel, cobalt and iron, respectively, Y is at least one element selected from the group of tin, zinc, tungsten, chromium, manganese, magnesium, antimony and titanium, Z is at least one element selected from the group of potassium, rubidium, thallium and cesium, and a, b, c, d, f, g, h and x represent the number of atoms of molybdenum, bismuth, nickel, cobalt, iron, Y, Z and oxygen, respectively, a=12, b=0.1 to 7, c+d=0.5 to 20, f=0.5 to 8, g=0 to 2, h=0 to 1 and x is determined by the oxidized condition of each element)
in the plural supported catalysts having different activities.

7. The method according to any one of claims 1 or 4 wherein the carrier of the plural supported catalysts having different activities is the same.

8. The method according to any one of claims 1 or 4 wherein the composition of the catalytically active component of the plural supported catalysts having different activities, is the same.

9. The method according to any one of claims 1 or 4 wherein an amount of the carrier of the plural supported catalysts having different activities is at least 20% by weight based on the sum of the weight of the supported catalysts.

10. The method according to any one of claims 1 or 4 wherein of the plural supported catalysts having different activities, the catalyst which are obtained by calcining at a lower temperature or whose supporting amount are higher, are arranged nearer said outlet.

11. The method according to claim 6, wherein the carrier of the plural supported catalysts having different activities is the same.

12. The method according to claim 6, wherein the composition of the catalytically active component of the plural supported catalysts having different activities is the same.

13. The method according to claim 6, wherein an amount of the carrier of the plural supported catalysts having different activities is at least 20% by weight based on the sum of the weight of the supported catalysts.

14. The method according to claim 6, wherein of the plural supported catalysts having different activities, the catalyst which are obtained by calcining at a lower temperature or whose supporting amount are higher are arranged nearer said outlet.

* * * * *